(12) United States Patent
Lee et al.

(10) Patent No.: US 9,090,635 B2
(45) Date of Patent: Jul. 28, 2015

(54) COPPER ORGANIC METAL, METHOD FOR PREPARING COPPER ORGANIC METAL AND COPPER PASTE

(71) Applicant: SAMSUNG ELECTRO-MECHANICS CO., LTD., Suwon (KR)

(72) Inventors: Kwi Jong Lee, Suwon (KR); Ji Han Kwon, Namyangju (KR); Dong Hoon Kim, Seongnam (KR)

(73) Assignee: SAMSUNG ELECTRO-MECHANICS CO., LTD., Suwon (KR)

(*) Notice: Subject to any disclaimer, the term of this patent is extended or adjusted under 35 U.S.C. 154(b) by 88 days.

(21) Appl. No.: 13/723,908

(22) Filed: Dec. 21, 2012

(65) Prior Publication Data

US 2013/0161571 A1 Jun. 27, 2013

(30) Foreign Application Priority Data

Dec. 27, 2011 (KR) .................. 10-2011-0143417

(51) Int. Cl.
| C07F 1/08 | (2006.01) |
|---|---|
| H01B 1/02 | (2006.01) |
| H01B 1/22 | (2006.01) |
| C07F 1/00 | (2006.01) |

(52) U.S. Cl.
CPC . *C07F 1/08* (2013.01); *C07F 1/005* (2013.01); *H01B 1/02* (2013.01); *H01B 1/22* (2013.01); *H01B 1/026* (2013.01)

(58) Field of Classification Search
None
See application file for complete search history.

(56) References Cited

U.S. PATENT DOCUMENTS

| 7,777,059 B2 | 8/2010 | Wittenbecher et al. | |
|---|---|---|---|
| 2011/0111138 A1* | 5/2011 | McCullough et al. | ........ 427/595 |

FOREIGN PATENT DOCUMENTS

| JP | 2002-329419 | 11/2002 |
|---|---|---|
| JP | 2007-321215 | 12/2007 |
| JP | 2008-13466 | 1/2008 |
| JP | 2009-074054 | 4/2009 |
| JP | 2010-188094 | 9/2010 |
| JP | 2012-046779 | 3/2012 |
| KR | 1990-0003510 | 5/1990 |
| KR | 10-2005-0101101 | 10/2005 |
| KR | 10-2005-0104357 | 11/2005 |
| KR | 10-0818195 | 3/2008 |
| WO | WO 2008/013002 | 1/2008 |
| WO | WO 2010/018782 | 2/2010 |

OTHER PUBLICATIONS

English text machine translation of JP 2007-321215 A to Ono et al., accessed on the JPO AIPN website on Nov. 14, 2014 and attached to the case file as a PDF.*

(Continued)

*Primary Examiner* — Harold Pyon
*Assistant Examiner* — Katie L Hammer

(57) ABSTRACT

Disclosed herein are a copper organic metal, a method for preparing a copper organic metal and a copper paste. The copper organic metal is constituted to combine a copper atom, [R—$CO_2$] and amine based ligand (L), thereby making it possible to be subjected to a low temperature sintering process and having an improved conductivity at the time of forming a conductive pattern as compared to the related art.

2 Claims, 2 Drawing Sheets

(56) References Cited

OTHER PUBLICATIONS

Japanese Office Action dated Apr. 22, 2014 in corresponding Japanese Patent Application No. 2012-282160.
Korean Notice of Allowance mailed Jan. 20, 2014 in corresponding Korean Application No. 10-2011-0143417.
Ligand—Wikipedia, the free encyclopedia, Feb. 13, 2015, http://en.wikipedia.org/wiki/Ligand (12 pages).
Amine—Wikipedia, the free encyclopedia, Feb. 13, 2015, http://en.wikipedia.org/wiki/Amine (13 pages).
Alkyl—Wikipedia, the free encyclopedia, Feb. 16, 2015, http://en.wikipedia.org/wiki/Alkyl (3 pages).
Hydroxyl—Wikipedia, the free encyclopedia, Feb. 16, 2015, http://en.wikipedia.org/wiki/Hydroxyl (3 pages).
Chinese Office Action issued Jan. 23, 2015 in corresponding Chinese Patent Application No. 2012105812181.
CA CAS RN. 1007348-38-0, SRN Registry, Mar. 11, 2008, pp. 1-4.

* cited by examiner

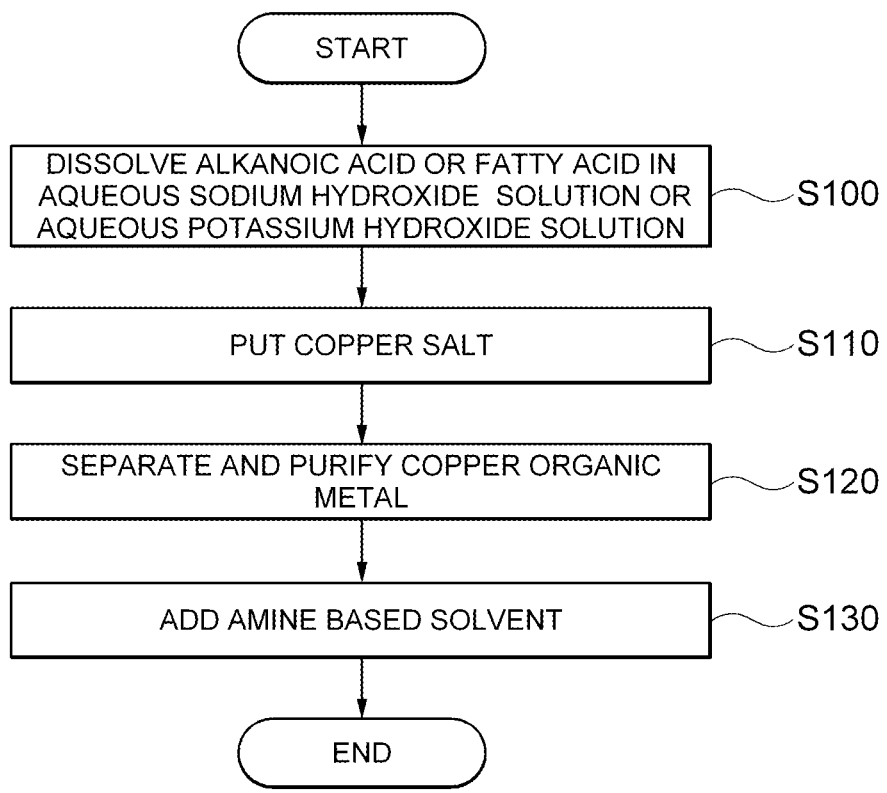

COPPER ORGANIC METAL, METHOD FOR PREPARING COPPER ORGANIC METAL AND COPPER PASTE

CROSS REFERENCE(S) TO RELATED APPLICATIONS

This application claims the benefit under 35 U.S.C. Section 119 of Korean Patent Application Serial No. 10-2011-0143417, entitled "Copper Organic Metal, Method for Preparing Copper Organic Metal and Copper Paste" filed on Dec. 27, 2011, which is hereby incorporated by reference in its entirety into this application.

BACKGROUND OF THE INVENTION

1. Technical Field

The present invention relates to a copper organic metal, a method for preparing a copper organic metal, and a copper paste.

2. Description of the Related Art

Copper has a specific resistance value similar to that of silver, but the material costs thereof are much less than silver, such that copper is currently used for electric wiring of most electronic components.

In the case of forming a copper paste using a copper powder, the copper powder is naturally oxidized or oxidized at the time of heat treatment during a sintering process, or the like, such that conductivity thereof is deteriorated.

Meanwhile, a technology of forming a paste using a nano-sized copper particle and forming a conductive pattern using the paste has been suggested.

As an example, Patent Document 1 discloses a technology in which a paste including nano-sized copper particles is sintered at about 350° C. to form a copper metal wiring.

In general, as a sintering temperature increases, oxidation of a metal is intensified, such that conductivity is reduced.

In order to overcome the reduction in conductivity at the time of the high sintering process as described above, Patent Document 2 discloses a technology of coating a surface of the copper particle with silver so as to lower the sintering temperature of the copper particle. However, additional preparing processes of coating silver are added, and material costs are increased.

In addition, in the case of forming the paste made of nano-sized metals of the related art, only a non-polar solution may be used. Other materials such as a binder, or the like, inserted in the process of forming the conductive pattern using the paste are soluble in a polar solvent. Therefore, since the paste including the nano-sized metal of the related art has a limitation in using of the solvent, the degree of freedom in designing of the paste composition is low in view of viscosity control, improvement in dispersibility, or the like of the paste composition.

SUMMARY OF THE INVENTION

An object of the present invention is to provide a copper organic metal capable of being subjected to a low temperature sintering process and having improved conductivity after the sintering process.

Another object of the present invention is to provide a copper organic metal having large degrees of freedom in its design.

Still another object of the present invention is to provide a method for preparing the copper organic metal.

Still another objection of the present invention is to provide a copper paste including the copper organic metal.

According to an exemplary embodiment of the present invention, there is provided a copper organic metal having a molecular structure expressed by formula 1 as follows:

[Chemical Formula 1]

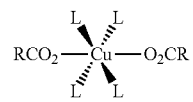

wherein R is an alkyl group and L is an amine based ligand.

In this case, the amine based ligand may include alkylamine.

In addition, the alkylamine may be any one material selected from $R-NH_2$, $R-NH-R'$ and $R_3-N$.

In addition, the amine based ligand may include hydroxyl (—OH) group.

In addition, the amine based ligand may include $HO-R-NH_2$.

Meanwhile, according to an exemplary embodiment of the present invention, there is provided a method for preparing a copper organic metal including: preparing a first solution by dissolving alkanoic acid or fatty acid in aqueous sodium hydroxide solution or aqueous potassium hydroxide solution; mixing the first solution and a second solution having a dissolved copper salt therein; and separating and purifying a copper organic metal from the mixed solution including the first solution and the second solution.

In addition, according to an exemplary embodiment of the present invention, there is provided a method for preparing a copper organic metal including: preparing a first solution by dissolving alkanoic acid or fatty acid in an aqueous sodium hydroxide solution or an aqueous potassium hydroxide solution; mixing the first solution and a second solution having a dissolved copper salt therein; separating and purifying a copper organic metal from the mixed solution including the first solution and the second solution; and reacting the separated and purified copper organic metal with amine based solvent.

The amine based ligand may include alkylamine.

The alkylamine may be any one material selected from $R-NH_2$, $R-NH-R'$ and $R_3-N$.

The amine based ligand may include hydroxyl (—OH) group.

The amine based ligand may include $HO-R-NH_2$.

According to an exemplary embodiment of the present invention, there is provided a copper paste prepared by mixing a general copper powder and the copper organic metal as described above.

BRIEF DESCRIPTION OF THE DRAWINGS

FIG. 3 is a flow chart showing a method for preparing the copper organic metal according to an exemplary embodiment of the present invention.

DESCRIPTION OF THE PREFERRED EMBODIMENTS

Figure 1:
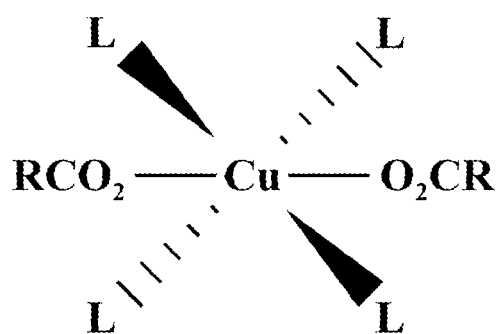
FIG. 1 is a view showing a molecular structure of a copper organic metal according to an exemplary embodiment of the present invention.

Various advantages and features of the present invention and methods accomplishing thereof will become apparent from the following description of embodiments with reference to the accompanying drawings. However, the present invention may be modified in many different forms and it should not be limited to the embodiments set forth herein. These embodiments may be provided so that this disclosure will be thorough and complete, and will fully convey the scope of the invention to those skilled in the art. Like reference numerals throughout the description denote like elements.

Terms used in the present specification are for explaining the embodiments rather than limiting the present invention. Unless explicitly described to the contrary, a singular form includes a plural form in the present specification. The word "comprise" and variations such as "comprises" or "comprising," will be understood to imply the inclusion of stated constituents, steps, operations and/or elements but not the exclusion of any other constituents, steps, operations and/or elements.

Hereinafter, a configuration and an acting effect of exemplary embodiments of the present invention will be described in more detail with reference to the accompanying drawings.

FIG. 1 is a view showing a molecular structure of a copper organic metal according to an exemplary embodiment of the present invention.

Referring to FIG. 1, the copper organic metal according to the exemplary embodiment of the present invention may include a copper atom and two [R—$CO_2$] ion-bonded thereto. Here, R means an alkyl group.

In addition, hydrophilicity may be increased or hydrophobicity may be increased depending on the number of carbons included in the alkyl group.

For example, in the case of applying the alkyl group having one carbon atom, affinity with water thereof is the largest and in the case of applying alkyl group having eight carbon atoms, affinity with alcohol thereof is increased.

In addition, L, which is an amine based ligand, is combined with the copper atom.

Here, the amine based ligand may be alkylamine or amines including a hydroxyl (—OH) group.

In addition, the alkylamine may be any one material selected from R—$NH_2$, R—NH—R' and $R_3$—N.

In addition, the amines including a hydroxyl (—OH) group may be HO—R—$NH_2$.

In the case in which the amine based ligand includes the alkylamine, the copper organic metal has good reactivity with a non-polar solvent.

In addition, in the case in which the amine based ligand is amine including a hydroxyl (—OH) group, the copper organic metal has good reactivity with a polar solvent.

Therefore, the copper organic metal according to another exemplary embodiment of the present invention may allow compatibility with the solvent of the copper organic metal to include polarity or a non-polarity by changing the kind of the amine based ligand, such that at the time of designing the metal paste, the degree of freedom may be increased.

Figure 2:
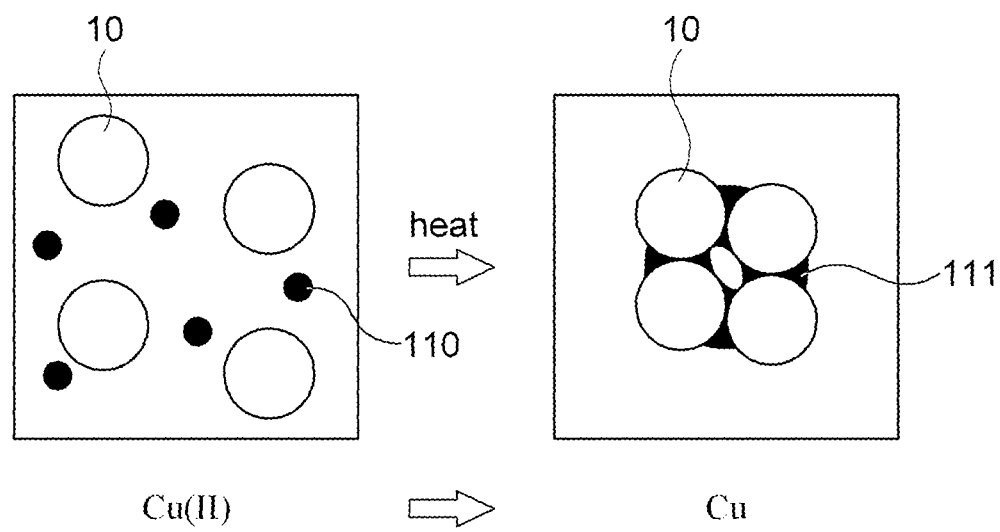
FIG. 2 is a view schematically showing a change of a particle state at the time of heating a paste in which a copper powder and the copper organic metal according to the exemplary embodiment of the present invention are mixed.

FIG. 2 is a view schematically showing a change in a particle state at the time of heating a copper powder and a paste mixed with the copper organic metal.

Referring to FIG. 2, in the case of forming the copper paste by mixing a general copper powder 10 and a copper organic metal 110 at a proper ratio, when applying heat below about 300☐, the copper organic metal 110 allows combinability among the copper powders 10 to be improved to thereby have improved conductivity.

In this case, while the copper organic metal is heated, the copper ion present in a state of Cu (II) in the copper organic metal is separated from R—$CO_2$ to be changed in a state of Cu atom, such that a conductive pattern is formed. Therefore, a sintering process being subjected at a temperature lower than the temperature of the related art is possible due to the reaction in which the copper ion is changed to the Cu atom.

In addition, in the case of combining the Cu atom with the amine based ligand, the amine based ligand is separated from the Cu atom due to the heating. In this case, when the amine based ligand is separated, a separation of R—$CO_2$ is promoted, such that a sintering temperature may be further lowered.

A general copper paste of the related art is constituted to include a copper powder and a binder. At the time of heating and firing it, copper particles may be combined to one another by the binders. However, since the general binders of the related art were all electrical nonconductors, conductivity was decreased in the case in which the binders were positioned among the copper particles.

In addition, the general copper paste of the related art was rapidly oxidized at the time of high temperature firing, such that an oxide film was formed on a surface of the copper particle, thereby decreasing conductivity.

However, the copper organic metal according to the exemplary embodiment of the present invention as described above may include the copper ion. As the sintering process progresses, the copper ion is changed to be the copper atom to be combined between the copper powders, such that conductivity may be improved as compared to the related art.

In addition, while R—$CO_2$ and the amine based ligand included in the organic metal according to the exemplary embodiment of the present invention are separated from the copper ion, oxides presented in the surface of the copper particle are removed, such that conductivity may be further improved.

Meanwhile, the copper paste according to the exemplary embodiment of the present invention may be formed by mixing the general copper powder and the copper organic metal as described above.

EXPERIMENTAL EXAMPLE 1

The copper pastes were prepared by varifying the contents of the copper powder and the copper organic metal, and each of the prepared copper pastes was subjected to the sinter process at 200☐ for 1 hour under nitrogen reduction atmosphere and then resistance thereof was measured.

Here, in order to prepare the copper paste, epoxy, ethyl cellulose, terpineol, and butyl carbitol acetate was used as the main binder and solvent.

TABLE 1

| Linear resistance according to content of copper organic metal | |
|---|---|
| Composition of copper paste (weight ratio of copper powder:copper organic metal) | Linear resistance ($\Omega$) |
| 100:0 | 300 |
| 95:5 | 140 |
| 90:10 | 12 |

Referring to Table 1, it may be appreciated that as the content of the copper organic metal is increased, linear resistance is remarkably decreased.

Meanwhile, as the content of the copper organic metal is increased, viscosity of the copper paste is increased. According to the limitation of the permissible density in a process of forming the conductive pattern, the content of the copper organic metal is preferably controlled.

FIG. 3 is a flow chart showing a method for preparing the copper organic metal according to the exemplary embodiment of the present invention.

Referring to FIG. 3, first, alkanoic acid or fatty acid is dissolved in aqueous sodium hydroxide solution or aqueous potassium hydroxide solution to prepare a first solution (S100).

Next, the first solution is mixed with a second solution having a dissolved copper salt therein (S110).

At this time, [R—$CO_2$] group included in the first solution and the copper atom included in the first solution are ion-bonded to each other, such that the copper organic metal is formed.

Next, the copper organic metal is separated and purified from the mixed solution including the first solution and the second solution (S120).

Thereafter, amine based solvent is added (S130).

That is, the separated and purified copper organic metal reacts with the amine based solvent, such that the copper atom is combined with the amine based ligand (L), thereby making it possible to complete the copper organic metal.

According to an exemplary embodiment of the present invention, the copper organic metal is capable of being subjected to a sintering process below 300□ under reduction atmosphere, and having improved conductivity after the sintering process as compared to that of the related art.

According to an exemplary embodiment of the present invention, the copper organic metal has compatibility with the polar solvent or the non-polar solvent, such that the metal paste including the copper organic metal has improved degrees of freedom in its design.

The present invention has been described in connection with what is presently considered to be practical exemplary embodiments. Although the exemplary embodiments of the present invention have been described, the present invention may be also used in various other combinations, modifications and environments. In other words, the present invention may be changed or modified within the range of concept of the invention disclosed in the specification, the range equivalent to the disclosure and/or the range of the technology or knowledge in the field to which the present invention pertains. The exemplary embodiments described above have been provided to explain the best state in carrying out the present invention. Therefore, they may be carried out in other states known to the field to which the present invention pertains in using other inventions such as the present invention and also be modified in various forms required in specific application fields and usages of the invention. Therefore, it is to be understood that the invention is not limited to the disclosed embodiments. It is to be understood that other embodiments are also included within the spirit and scope of the appended claims.

What is claimed is:

1. A copper organic metal having a molecular structure expressed by formula 1 below:

[Chemical Formula 1]

wherein R is an alkyl group and L is an amine based ligand including a hydroxyl group, and wherein nitrogen of the amine based ligand is bonded with the Cu of the Chemical Formula 1.

2. A copper organic metal having a molecular structure expressed by formula 1 below:

[Chemical Formula 1]

wherein R is an alkyl group and L is HO—R—$NH_2$, and wherein nitrogen of the HO—R—$NH_2$ is bonded with the Cu of the Chemical Formula 1.

* * * * *